(12) United States Patent
Morgan et al.

(10) Patent No.: US 6,399,045 B1
(45) Date of Patent: *Jun. 4, 2002

(54) LIQUID SUNSCREEN COMPOSITIONS WHICH BOTH DEPOSIT AND LATHER WELL

(75) Inventors: Leslie Jo Morgan, Chatham, NJ (US); Sudhakar Puvvada, Shelton, CT (US); Liang Sheng Tsaur, Norwood, NJ (US); Michael Paul Aronson, West Nyack; Andrew Lam, Yorktown Heights, both of NY (US); Shiji Shen, Norwood; Ernest Weatherley Macaulay, Morris Township, both of NJ (US)

(73) Assignee: Unilever Home & Personal Care USA a division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/523,131

(22) Filed: Mar. 10, 2000

Related U.S. Application Data

(63) Continuation-in-part of application No. 09/298,580, filed on Apr. 23, 1999, now Pat. No. 6,224,852.

(51) Int. Cl.$^7$ .............................. A61K 7/42; A61K 7/44; A61K 7/06; A61K 7/11; A61K 7/075

(52) U.S. Cl. .................. 424/59; 424/70.1; 424/70.9; 424/70.11; 424/70.19; 424/70.22; 424/401; 424/60; 510/130; 510/135; 510/136; 510/137; 510/138; 510/158; 510/159; 514/846; 514/944; 514/945

(58) Field of Search .................. 424/401, 50, 60, 424/70.1, 70.9, 70.11, 70.19, 70.22; 510/130, 135, 136, 137, 138, 158, 159; 514/846, 944, 945

(56) References Cited

U.S. PATENT DOCUMENTS

| 3,580,853 A | 5/1971 | Parran, Jr. |
| 3,753,916 A | 8/1973 | Parran, Jr. |
| 4,701,321 A | 10/1987 | Bernstein |
| 4,933,174 A | 6/1990 | Bernstein |
| 4,948,576 A | 8/1990 | Verdicchio et al. |
| 5,186,928 A | 2/1993 | Birtwistle |
| 5,223,250 A | 6/1993 | Mitchell et al. |
| 5,348,736 A | 9/1994 | Patel et al. |
| 5,476,660 A | 12/1995 | Somasundaran et al. |
| 5,543,074 A | 8/1996 | Hague et al. |
| 5,726,138 A | 3/1998 | Tsaur et al. |
| 5,804,538 A | 9/1998 | Wei et al. |
| 5,912,002 A | 6/1999 | Grieveson et al. |
| 5,929,019 A | 7/1999 | Puvvada et al. |
| 6,156,713 A * | 12/2000 | Chopra et al. ............... 510/130 |
| 6,224,852 B1 * | 5/2001 | Morgan et al. ............... 424/59 |

FOREIGN PATENT DOCUMENTS

| EP | 0117135 | 8/1984 |
| EP | 0313303 | 4/1989 |
| EP | 0386898 | 9/1990 |
| EP | 0552024 | 7/1993 |
| WO | 95/22311 | 8/1995 |
| WO | 95/28912 | 11/1995 |
| WO | 96/02229 | 2/1996 |
| WO | 96/02230 | 2/1996 |
| WO | 99/13854 | 3/1999 |

* cited by examiner

Primary Examiner—Jose G. Dees
Assistant Examiner—Marina Lamm
(74) Attorney, Agent, or Firm—Ronald A. Koatz

(57) ABSTRACT

The present invention teaches liquid sunscreen compositions in which level of surfactant is higher than level at which the sunscreen component(s) are still soluble in the surfactant in which they are used; and which comprise minimal levels of cationic polymer. Combination of cationic polymer (especially preferred surfactants and at minimum levels) and minimal levels of sunscreen lead to compositions with minimal levels of deposition and minimal SPF. Further, the compositions also maintain good lather.

17 Claims, No Drawings

LIQUID SUNSCREEN COMPOSITIONS
WHICH BOTH DEPOSIT AND LATHER
WELL

RELATED APPLICATIONS

The subject application is a continuation-in-part application of U.S. Ser. No. 09/298,580, filed Apr. 23, 1999, now issued as U.S. Pat. No. 6,224,852 to Morgan et al.

FIELD OF THE INVENTION

The invention relates to liquid personal wash compositions comprising a sunscreen component and minimal required levels of cationic polymer. The compositions provide high deposition of sunscreen component; good SPF ("sun protection factor") values as defined in applicants' SPF tests; and good consumer acceptable levels of lather.

BACKGROUND OF THE INVENTION

It is extremely difficult to provide liquid personal wash compositions with sunscreen components or agents which sunscreen components may be readily deposited on the skin or other surface. One significant problem is that the sunscreen agents will generally be solubilized by the surfactant and, while they may be deposited during lathering, they will be removed by rinsing.

The art does teach use of certain cationic polymers to enhance deposition of sunscreen materials onto the hair and protect from harmful effects of sunlight. U.S. Pat. No. 5,186,928 to Birtwistle, for example, teaches use of a cationic derivative of polygalactomannan gum for such purpose. The level of sunscreen is never at such a high level, however, that the sunscreen will not solubilize in surfactant solution (column 2, lines 54–57). By contrast, sunscreens of the invention are used in concentrations above their solubility limit in the surfactant system in which they are used at least in part to ensure minimum levels of deposition.

EP Publication 552024 to Unilever is also concerned with enhancing deposition of cosmetic agents, including sunscreens. Here, an additional oil phase is added in order to reduce solubilization of the oil/sunscreen into the surfactant phase thereby allowing more sunscreen to be available for deposition upon rinsing. The subject invention, by contrast, does not rely on an oil carrier to enhance deposition (the oil is said to reduce solubility of component in surfactant phase and thus enhance deposition). Further the subject invention requires use of relatively high levels of cationic polymer to both enhance deposition of sunscreen (sunscreens being used at much higher levels than those used in U.S. Pat. No. 5,186,928 noted above) and increase SPF ("sun protection factor").

EP 313,303 (assigned to Procter & Gamble) discloses compositions comprising tocopherol sorbate (antioxidant) which may be used in combination with sunscreen agents. The compositions must also comprise anti-inflammatory agent and topical carrier. There is no recognition from this reference of using cationic polymer to enhance sunscreen deposition, particularly in formulations containing high amounts of sunscreen.

U.S. Pat. Nos. 4,701,321 and 4,933,174 to Bernstein teach method of using liquid detergent with sunscreen agent. The compositions contain only nonionic and amphoteric surfactants, unlike the cleansing compositions of the invention which must contain at least 5% anionic.

WO 99/13854 (assigned to Colgate) discloses a skin cleansing, sun protecting composition comprising (a) a sun protection hydrophobic agent; (b) a polar organic solvent less polar than water; (c) oil; and (d) cleansing effective amount of surfactant or mixture thereof wherein oil/polar solvent ratio is 1:4 to 1:0.8. In contrast to the aqueous systems of the subject invention, this is a non-aqueous system (see bottom of page 11).

Other references teach compositions which may contain surfactant, N-polymer and benefit agent (e.g., U.S. Pat. No. 4,948,576 to Verdiccio et al.; EP 117,135). These references fail to focus on sunscreens and/or to teach or suggest that sunscreens must be used in amounts beyond their solubility limit in the surfactant systems in which they are used; and that, when sunscreen is used in such large amounts, cationic polymer (at relatively large levels) both enhances deposition and SPF values.

BRIEF DESCRIPTION OF THE INVENTION

Unexpectedly, applicants have now discovered that minimum required levels of cationic polymer can be used to deposit sunscreen even in compositions comprising sunscreen at levels beyond their solubility limit in the surfactant system in which the sunscreen is found. This combination of high levels of sunscreen and cationic (as noted it was never previously recognized cationics could be used to provide enhanced effect even when such large amounts of sunscreen are used) leads not only to deposition of much greater amounts of sunscreen (at least 10 $\mu$g/cm$^2$), but to enhanced SPF (at least 2). Further, compositions have lather of greater than 70 ml (using funnel test) and are good cleansing compositions. In some embodiments, crystallization control agents suppress crystallization of sunscreen component(s) and may help enhance deposition even further.

More specifically, compositions of the invention are opaque (less than 50% transmittance at a visible wavelength) personal wash cleansing compositions comprising:

(a) 5% to 70% by wt. of a surfactant or surfactants selected from the group consisting of anionic, nonionic, amphoteric or zwitterionic and cationic surfactants wherein at least one surfactant is an anionic surfactant comprising at least 3% by wt., preferably at least 5%, more preferably at least 7% by wt. of total composition;

(b) 0.5 to 5% by wt. of a cationic polymer;

(c) 1% to 35% by wt. of a sunscreen or mixture of sunscreens;

wherein concentration of sunscreen component (c) is above the solubility limit of the sunscreen component in the surfactant system in which said sunscreen component is used;

wherein the composition has SPF factor of at least 2, preferably 2.5, more preferably 3.0;

wherein the sunscreen has deposition of at least 10 $\mu$g/cm$^2$ preferably at least 15 $\mu$g/cm$^2$, more preferably at least 20 $\mu$g/cm$^2$; and wherein composition has lather volume of greater than 70 ml using funnel test.

DETAILED DESCRIPTION OF THE INVENTION

The present invention relates to opaque (less than 50% transmittance at visible wavelength) personal wash cleansing composition comprising (percent by weight).

(a) 5% to 70%, preferably 7% to 60% of a surfactant or surfactant selected from the group consisting of anionic, nonionic, amphoteric, zwitterionic and cationic surfactants wherein at least one surfactant is an anionic surfactant comprising at least 3% weight by weight, preferably at least 5%, more preferably at least 7% of total composition;

(b) 0.5, more preferably at least 1.0% by wt. to 5% cationic polymer. Preferably the polymer is a cationically modifier guar (e.g. cationic derivative of guar);

(c) 1% to 35% preferably 3% to 30%, more preferably 5% to 30% sunscreen or mixture of sunscreens;

wherein concentration of sunscreen component (c) is above the solubility limit of the sunscreen component in the surfactant system in which said sunscreen component is used;

wherein the composition has SPF factor of at least 2;

wherein the sunscreen has deposition of at least 10 $\mu g/cm^2$; and wherein composition has lather volume of greater than 70 ml using funnel test.

Surfactants

The surfactants of the invention may be chosen from the group consisting of anionic, nonionic, amphoteric/zwitterionic, cationic surfactants and mixtures thereof.

Examples of anionic surfactants are soap and anionic non-soap surfactants that can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art for example, sulfosuccinates, sarcosinates, taurates, phosphate and those listed in the *McCutcheon's Encyclopedia of Surfactants*.

The anionic surfactant must comprise at least 3% weight by weight of the compositions of the invention, preferably at least 5%, more preferably at least 7% by wt.

Additionally, nonionic surfactants can also be present in the composition alone or together with anionic or other surfactants to provide a cleansing and mildness effect. Typical examples of such nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

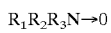

$R_1R_2R_3N\rightarrow 0$ wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$R\ R'R''P\rightarrow 0$ wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecylmethyl sulfoxide, 3-hydroxytridecyl methyl sulfoxide, 3-hydroxy-4-dodecoxybutyl methyl sulfoxide.

Although not necessary, other surfactants may be present in the composition. Examples of these surfactants include zwitterionic surfactants which can be exemplified by those which can be broadly described as derivatives of aliphatic quaternary ammonium, phosphonium, and sulfonium compounds in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

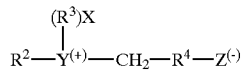

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus and sulfur atoms; $R^3$ is an alkyl or monohydroxyalkyl group containing 1 to about 3 carbon atoms; X is 1 when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; and 5-[S-3-hydroxypropyl-S-hexadecylsulfonio]-3 hydroxypentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072. N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines and amphoacetates are also useful in the present composition.

Examples of betaines useful herein include the high alkyl betaines such as coco dimethyl carboxymethyl betaine, lauryl dimethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydroxypropyl) alpha-carboxyethyl betaine etc. The sulfobetaines may be represented by coco dimethyl sulfopropyl betaine, stearyl dimethyl sulfopropyl betaine, amido betaines, amidosulfobetaines, and the like.

An example of amphoacetate is alkali metal alkyl amphoacetate.

Many cationic surfactants are known to the art. By way of example, the following may be mentioned:

stearyldimethylbenzyl ammonium chloride;
dodecyltrimethylammonium chloride;
nonylbenzylethyldimethyl ammonium nitrate;
tetradecylpyridinium bromide;
laurylpyridinium chloride;
ucetylpyridinium chloride;
laurylpyridinium chloride;
laurylisoquinolium bromide;
ditallow(Hydrogenated)dimethyl ammonium chloride;
dilauryidimethyl ammonium chloride; and
stearalkonium chloride.

Additional cationic surfactants are disclosed in U.S. Pat. No. 4,303,543, see column 4, lines 58 and column 5, lines 1–42, incorporated herein by references. Also see *CTFA Cosmetic Ingredient Dictionary*, $4^{th}$ Edition 1991, pages 509–514 for various long chain alkyl cationic surfactants; incorporated herein by references.

Cationic Polymer

A second critical component of the subject invention is use of cationic polymer. It is use of cationic polymer, particularly when amounts of sunscreen in excess of their solubility limit in the surfactant system carrying them are used, which is believed to lead to enhanced deposition of sunscreen as well as enhanced SPF.

Various cationic polymers may be used. Examples of cationic polymers include the cationic cellulose ethers described in U.S. Pat. Nos. 3,816,616 and 4,272,515 and which are available commercially from Union Carbide Corp. under the trademark POLYMER JR. Other suitable materials are the cationic polygalactomannan gum derivatives described in U.S. Pat. No. 4,298,494 which are commercially available under the trademark JAGUAR from Celanese-Stein Hall. An example of a suitable material is the hydroxypropyltrimethylammonium derivative of guar gum of the formula:

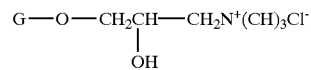

where G represents guar gum. Such a material is available under the name JAGUAR C-13-S. This material also has the CTFA designation Guar Hydroxypropyltrimonnium Chloride. In JAGUAR C-13-S the degree of substitution of the cationic groups is about 0.13. Another possible material is that known as JAGUAR C-17 which is similar to JAGUAR C-13-S but has a higher degree of substitution of cationic groups of about 0.25–0.31. A further example of a guar derivative is the hydroxypropylated cationic guar derivative known as JAGUAR C-16 which as well as containing the above cationic quaternary ammonium groups also contain hydroxypropyl (—CH$_2$CH(OH)CH$_3$) substituent groups. In JAGUAR C-16 the degree of substitution of the cationic groups is 0.11–0.16 and the moles of substitution of hydroxypropyl groups is 0.8–1.1.

Other cationic polymers include cationic polyamide polymers such as the low molecular weight adipic acid/ diethylene-triaminepolyamide and the copolymers of vinylpyrrolidone and dimethylaminoethyl methacrylate quaternized with dimethyl sulphate (Gafquat 744, GAF Corporation) described in U.S. Pat. No. 4,080,310; the graft cationic copolymer containing N-vinylpyrrolidone, dimethylaminoethyl methacrylate and polyethylene glycol described in U.S. Pat. No. 4,048,301; mineral acid salts of the amino-alkyl esters of homo- and copolymers of unsaturated carboxylic acids having from 3 to 5 carbon atoms described in U.S. Pat. No. 4,009,256; and the polymers of esterified starch described in U.S. Pat. No. 3,186,911.

The high molecular weight cationic polymers are sold under the trademark MERQUAT by Merck & Co., Inc. Representative polymers include Merquat 100, a highly charged cationic dimethyidiallylammonium chloride homopolymer, and Merquat™ 550, a highly charged cationic copolymer prepared with dimethyidiallylammonium chloride and acrylamide. These materials are designated in the CTFA dictionary as Quaternium-40 and Quaternium-41, respectively.

Especially preferred cationic polymers include the Jaguar type polymers noted above.

The cationic polymers should be 0.5 to 5% wt. parts, preferably 1 to 3%.

Sunscreen

Suitable sunscreen agents which may be used are disclosed for example in Segarin et al., chapter VIII, pages 189 of Cosmetics Science and Technology.

Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropylene glycol esters); Cinnamic acid derivatives (methyl and benzyl esters, alpha-phenyl cinnamonitrile; butyl cinnamoyl pyruvate); Dihydroxycinnamic acid derivatives (umbelliferone, methylumbelliferone, methylacetoumbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,3-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxalole, various aryl benzothiazoles); Quinine salts (bisulfate, sulfate, chloride, oleate, and tannate); quinoline derivatives (8-hydroxyquinoline salts, 2-phenylquinoline); Hydroxy-or methoxy substituted benzophenones; Uric and vilouric acids; Tannnic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyhldibenzoylmethane; Butylmethoxydibenzoylmethane; Etocrylene; and 4-isopropyl-di-benzoylmethane.

Of these, Octylmethoxycinnamate (2 ethyl hexyl methoxycinnamate), Avobenzone (4-tert-Butyl-4'-methoxydibenzoylmethane), Benzophenone-3 (2-Hydroxy-4-Methoxybenzophenone), Octyl dimethyl p-aminobenzoic acid, 2,2-di-hydroxy-4-Methoxybenzophenone, ethyl-4-[bis (hydroxypropyl)]aminobenzoate, Octocrylene (2-Ethylhexyl 2-Cyano-3,3-Diphenylacrylate), Octyl Salicylate (2-Ethylhexyl Salicylate), glyceryl aminobenzoate, 3,3,5-trimethylcyclohexylsalicylate, methyl anthranalite, p-dimethylaminobenzoic acid or aminobenzoate, 2-ethyl hexyl p-dimethyl aminobenzoate, 2-phenyl benzimidazole-5-sulfonic acid and mixtures of these compounds are particularly useful.

Preferred Sunscreens useful in the compositions of the present invention are Octylmethoxycinnamate (ethyl hexyl methoxycinnamate), also known as Parsol MCX or Univol, Octocrylene (2-Ethylhexyl 2-Cyano-3,3-Diphenylacrylate), Octyl Salicylate (2-Ethylhexyl Salicylate), Benzophenone-3 (2-Hydroxy-4-Methoxybenzophenone), and Avobenzone (4-tert-Butyl-4'-methoxydibenzoylmethane).

The sunscreen or mixture should be used at 1% to 35 wt. parts of the composition, preferably 3 to 30 wt. parts, more preferably 5 to 25 wt. %.

The combination of sunscreen should be chosen, however, such that the amount of sunscreen(s) is above the solubility limit of the sunscreen component in the surfactant system in which the sunscreen(s) is used. For example, if a sunscreen has a solubility limit of 3% in a surfactant mixture, there must be more than 3% of such sunscreen in the composition.

The sunscreen should further be used in an amount sufficient to provide SPF at least 2, preferably at least 2.5, more preferably at least 3.0.

SPF is a commonly used measure of photo protection of a sunscreen against erythema. This number is derived from another parameter, the minimal erythemal dose (MED). MED is defined as the "least exposure dose at a specified wavelength that will elicit a delayed erythema response." The MED indicates the amount of energy irradiating the skin and the responsiveness of the skin to the radiation. The SPF of a particular photo protector is obtained by dividing the MED of protected skin by the MED of unprotected skin. The higher the SPF, the more effective the agent in preventing sunburn. The SPF value tells how many times longer a person can stay in the sun person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. Typically, commercially available sunscreening products have SPF values ranging from about 2 to 45.

The value of at least 2 is determined using method described in protocol of the application.

Together the amount of sunscreen and amount of cationic polymer must be sufficient such that there is deposition of at least 10 μg/cm$^2$.

Compositions of the invention must also be able to provide foam height of at least 70 ml, preferably 80–1000 ml, more preferably at least 110 ml, more preferably greater than 200 ml and more preferably more than 250 ml using the funnel test described in the protocol.

Finally, compositions of the invention are opaque as defined above.

It should be understood that variables may vary depending on exact compositions. Thus, compositions with more cationic (e.g., 1% or more) will tend to have higher deposition or those with specific polymer may deposit better than others. Also, the higher level of sunscreen, the greater the tendency that more of it will be above the solubility of surfactant system in which it is used and thus will deposit better. All these factors should be taken into account when designing optimal compositions.

Compositions of the invention may be shampoos, shower gel, handwash, face and body wash or other similar types of compositions. Generally, they will comprise at least 30% parts weight, preferably 35–90% water. Viscosity of compositions may range from 10,000 to 300,000 using a T-bar Spindle A at 0.5 rpm (about 25° C.) or 500–30,000 cps using Brookfield Spindle 5 at 20 rpm (about 25° C.).

Optionals

The present invention provides compositions may utilize about 1.0% to 15% by wt., preferably 1 to 10% by wt. of a structuring agent which works in the compositions to form a lamellar phase.

Where the composition is not lamellar structured and enhanced particle suspension is desired, it is usually necessary to add external structurants such as carbomers (e.g., cross-linked polyacrylate such as Carbopol$^{(R)}$) and clays.

Lamellar structurant may include fatty acid such as lauric acid, isostearic acid, oleic acid or ester derivative thereof; and/or unsaturated and/or branched long chain liquid alcohol or ether derivatives thereof.

Examples of alcohols include oleyl alcohol and isostearyl alcohol. Examples of ether derivatives include isosteareth or oleth carboxylic acid; or isosteareth or oleth alcohol.

The structurant may also be trihydroxystearin.

The invention may also comprise oil/emollient particles.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil, and avocado oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acetylated lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include aloe vera, mineral oil, petrolatum, silicone oil such as dimethyl polysiloxane, lauryl and myristyl lactate.

The emollient/oil is generally used in an amount from about 1 to 50%, preferably 1 to 30% by wt. of the composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil$^{(R)}$ from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and Vitamin A, C & E or their derivatives may be used advantageously in amounts of about 0.01% or higher if appropriate.

Polyethylene glycols which may be used include:

| | | |
|---|---|---|
| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm$^{(R)}$ (PEG modified glyceryl cocoate, palmate or tallowate) from Rewo Chemicals; Antil$^{(R)}$ 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut sheets and apricot seeds.

Another preferred ingredient is a crystallization suppressant or control agent which is used to suppress individual or mixtures of sunscreen ingredients from crystallizing out of solution. This may lead to reduced deposition. These suppression agents include, for example, organic esters such as $C_{10}$–$C_{24}$, preferably $C_{12}$–$C_{15}$ alkyl benzoate among others. Other examples include Bernel PCM from Bernel, and Elefac 205 from Bernel. Specific sunscreen(s) are more resistant to crystallization than others, e.g., butyl octyl salicylate.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

The following protocols were used in making deposition and SPF measurements discussed in the examples.

SPF Test Method

The protocol used to test the prototypes for Sun Protection Factor (SPF) on humans is described below:

Panel

Panelists are selected by good clinical practice inclusion criteria among which are: 18 years of age or older, with fair skin of types I, II or III, free of any dermatological or systemic disorder which would interfere with the results, be screened according to a preliminary medical history, have no known abnormal response to sunlight, have signed an informed consent. The skin types are defined as follows:

I: always burns easily; never tans

II: always burns easily; tans minimally

III: burns moderately; tans gradually

Exclusion criteria include, under a doctor's care, taking medication which may interfere with the results, with chronic skin allergies, with suntan or sunburn, pregnant or lactating females.

Light Source

The light source employed is a 150 watt Xenon Arc Solar Simulator having a continuous emission spectrum in the UV-B range form 290 to 320 nm. Xenon arc is selected on the basis of its black body radiation temperature of 6000° K. which produces continuous UV spectra (all wavelengths) substantially equivalent to that of natural sunlight.

This device is equipped with a dichroic mirror (which reflects all radiation below 400 nm) and works in conjunction with a 1 mm thick Schott WG-320 filter (which absorbs all radiation below 290 nm) to produce simulation of the solar UVA-UVB spectrum. A 1 mm thick UG 5 or UG 11 filter (black lens) was added to remove reflected (infra-red, greater than 700 nm) heat and remaining visible radiation.

UVB radiation was monitored continuously during exposure using a Model DCS-1 Sunburn UV Meter/Dose Controller System (Solar Light Co.) formerly known as the Robertson-Berger Sunburn meter (R-B meter). Measurements were taken at a position within 8 mm from the surface of the skin. The field of irradiation was 1 cm in diameter.

Procedure

One test site area served to determine each subject's Minimal Erythema Dose (MED). This was executed by exposing the back to a series of timed incremental UV exposures at 25% intervals. The individual subject's MED is the shortest time of exposure that produces minimally perceptible erythema at 20 to 24 hours post irradiation. The test area is described as the infra capsular area of the back to the right and left of the midline.

In an uninvolved area, two sites were marked for unprotected control and homosalate control product and control product was applied. The homosalate standard was delivered to the test site through a plastic volumetric syringe. The material was then evenly applied to a rectangular area measuring 5 cm×10 cm (50 cm$^2$) for a final concentration of 2.0 mg/cm$^2$. Fifteen (15.0) minutes after application, a series of UV light exposures in 25% increments, calculated from previously determined MED's, bracketing the intended SPF was administered from the solar simulator to sub sites within the treated area. On the actual day of testing another series of exposures similar to the one given on the previous day was administered to an adjacent untreated, unprotected area of the skin to re-determine the MED.

An adjacent test site was then selected to perform an SPF determination of the test substance. A 5×10 cm$^2$ target area was marked on the back and centered within an 8×16 cm oval. The oval was 100 cm$^2$ and defined as the lather area. The test panelist stood in the tub area and the back was not immersed, however, it was maintained in a vertical position. A hand held sprayer with a water temperature of 25–30° C. and a flow rate of ~13 ml/sec was used. Sprayer was held at a 45° angle to the back and a distance of 6 inches from the back and aimed at a site 8 inches above the center of the target area. The spray was maintained for 15 seconds allowing water to run down over the lather area.

0.1 ml of product was applied using a plastic volumetric syringe across the wet target area. The site was lathered by a technician with the index and middle finger in a circular motion over the entire target area, making sure to have uniform lathering over the entire site. Lathering was conducted for 15 seconds without spray. While the technician continued to rub/lather, a rinsing spray was reintroduced for 10 seconds in the manner described above. Lathering was ceased and the site was sprayed for another 5 seconds. A terrycloth towel was folded so as to cover the entire lather area. The site was gently patted dry 4 times in a blotting motion.

The above described procedure was repeated for the test material on the opposite side of the back. Sites were allowed to re-equilibrate for 30 minutes after rinse procedure. The sites were irradiated as described above.

Evaluation of Responses

The panelists were instructed to return to the testing facility 20 to 24 hours post exposure for evaluation of delayed erythemic response. The smallest exposure or the least amount of energy required to produce erythema (MED) in the treated site was recorded. The SPF was then calculated, according to the following equation:

$$SPF = \frac{\text{MED Protected Skin}}{\text{MED Unprotected Skin}}$$

All expert graders are required to take and pass a visual discrimination examination conducted by a Board Certified Ophthalmologist using the Farnsworth-Munsell 100 Hue Test as published which determines a person's ability to discern color against a black background. This test was additionally modified to include a flesh tone background more nearly approaching actual use conditions, wherein erythematous skin is graded according to intensity.

Panelist's results were rejected if:

1. The responses on the treated site were randomly absent or out of sequence. This was an indication that the products were not spread uniformly.
2. An MED could not be obtained due to elicited response at all exposure sites.
3. The exposure series failed to elicit an MED response on either the untreated or the applied skin areas. The test was then considered a technical failure and the subject's data discarded.

In-vitro Deposition Method

The method used to quantify the in-vitro deposition of sunscreen from prototypes is described below. Assays are done in triplicate to obtain an average of the deposition measurement for each prototype.

Skin Preparation

Juvenile female porcine skin (3–4 weeks old) is purchased and prepared for use by shaving and pre-washing. Hair was shaved with a Norelco electric razor, Model 715RL. The skin was pre-washed with 5 ml of 5% NaLES surfactant solution and rinsed well with water. Three replicate pre-wash treatments were performed to remove triglycerides and alkanes present on the skin as natural components. The skin was then cut into approximately 3"×3" to obtain 18–21 pieces of skin. The pre-washed shaved porcine skins were placed randomly in aluminum foil and stored in the freezer with an assigned batch number.

Treatment with Prototype

A piece of pre-washed porcine skin sample was thawed, rinsed once with warm tap water with a controlled flow rate of ~130 mL–140 ml/10 seconds to wet the surface of the skin. Excess water was allowed to drip from the skin. The pre-washed skin was treated with a cleanser prototype using 0.5 g/58 cm² skin area. Product is lathered/rubbed onto the skin in a circular motion to ensure even coverage for 15 seconds which is about 20 times of rubbings. The skin was then rinsed with tap warm water using the above flow rate for 15 seconds. The skin was patted once with paper towel to dry and placed in hood to allow further drying for 5 minutes.

Extraction and Quantification of UV Absorber

Extraction of the skin benefit agents on the cleansed porcine skin was performed using 10 mL of heptane, 5.0 cm diameter hollow glass cylinder and a disposal pipetter. Two extractions were carried out on each porcine skin sample. The glass cylinder was placed onto the skin and held tightly to create a good seal on the porcine skin. The disposal plastic pipette was used to provide some mixing of the heptane during extraction. Each extraction was performed using about 5 mL of heptane for 2 minutes and 40 seconds. The heptane extracts were combined and collected into a vial. The weight of the heptane extract was recorded. Quantification relies on uv spectrophotometry comparing absorbance spectrum of the extract against that for calibration standards.

Lather Volume

Lather volume was measured using a pouf method. Lather was generated by dispensing 1 gram of product onto a wet (drained) pouf, which was then squeezed uniformly for 30 times with one hand. The pouf was gently immersed into water (90° F.) and the generated lather was collected in a graduated tube through a funnel with a big mouth. Its volume was calculated by the difference of the readings between the top and the bottom. The measurement was repeated 7 times for each sample.

Preparation

Typically, examples of the invention were made as follows:

Required water was added to the mixing tank and heated to 75° C. Anionic surfactants were added (one at a time if a mixture) and stirred until completely dissolved. Amphoteric surfactants were added and stirred until completely dissolved. Sunscreen pre-mix was charged and mixed until thoroughly dispersed. Glycerin/cationic polymer pre-mix was charged and mixed thoroughly. Cooling was begun and optional ingredients (e.g., opacifier, preservative, perfume, etc.) were added.

The two pre-mixes were prepared:

(i) Pre-mix of cationic polymer in glycerin;

(ii) UV absorbers were thoroughly mixed assuming complete dissolution; heat was used if necessary. Crystallization control agent was also used, if required.

The following examples were made which show the use of various sunscreen levels and combinations.

Example 1

Solubility Limits of Constant Sunscreen Mixture in Different Surfactant Systems

TABLE 1

Solubility of 7.5/6/5 - MCX/BP3/OS in Surfactant Mixtures:

| Surfactant | Sunscreen Solubility Limit, % |
|---|---|
| 8/3.5/3.5-Betaine/Sodium Isethionate (SI)/Sodium Laureth Ether Sulfate (SLES) | 2–2.3% |
| 10/5-Betaine/SLES | 1–1.5% |
| 5/10 - Betaine/Genapol AMS | 1–1.5% |
| 10/5-Betaine/SLES + 1% Perfume | ~3% |

MCX = Octyl Methoxy Cinnamate
BP3 = Benzophenone 3
OS = Octyl Salicylate
Genapol AMS = Acylaminopolyglycol ether sulfate triethanolamine salt Table 1 shows how much of a given sunscreen mixture (MCX/BP3/OS) can be solubilized in various surfactant systems.

According to the invention, the sunscreen or mixture must be above its solubility limit in a given system to achieve enhanced deposition.

Example 2

TABLE 2

Solubility of Different Sunscreen Systems in Constant Surfactant System (8/3.5/3.5 - Betaine/SI/SLES):

| Sunscreen Mixture | Sunscreen Solubility Limit, % |
|---|---|
| 7.5/6/5 - MCX/BP3/OS | 2–2.3% |
| 7.5/6 10 - MCX/BP 3/OC OS | 2–2.5% |
| | 2–2.5% |
| MCX | 1.–2.5% |
| OC (Octycrylene) | 0.8–1.3% |

Table 2 above shows that, within a given surfactant system, the solubility limit will vary depending on which sunscreen or sunscreen mixture is used. Thus, for example, enhanced deposition of OC can occur at lower level of OC than enhanced deposition of OS in the same system.

Examples 3–5 and Comparative

TABLE 3

Formulate above solubility limit to ensure adequate deposition.

| | 3<br>18.5%<br>Sunscreen | 4<br>13.0%<br>Sunscreen | 5<br>9.0%<br>Sunscreen | Comparative<br>Solubilized by<br>the Surfactant<br>3.0% Sunscreen |
|---|---|---|---|---|
| Cocoamido Propyl Betaine | 8.0 | 8.0 | 8.0 | 10.0 |
| Sodium Cocoyl Isethionate | 3.5 | 3.5 | 3.5 | |
| Sodium Laureth Sulfate | 3.5 | 3.5 | 3.5 | 5 |
| Octyl Methoxy Cinnamate (MCX) | 7.5 | 5.3 | 3.7 | 3.0 |
| Benzophenone-3 (BP3) | 6.0 | 4.2 | 2.9 | |
| Octyl Salicylate (OS) | 5.0 | 3.5 | 2.4 | |
| Octycrylene (OC) | | | | |
| Avobenzone | | | | |
| Crystallization Control Agent | 4.0 | | | |
| Guar Hydroxypropyl Trimonium Chloride | 1.6 | 1.6 | 1.6 | 1.5 |
| Glycerol | 6.0 | 6.0 | 6.0 | 5.0 |
| Perfume | 1.0 | 1.0 | 1.0 | 1.0 |
| Water | To 100% | To 100% | To 100% | To 100% |
| Deposition | 53 | 50 | 46 | 7 |

The examples above show that, where level of sunscreen (18.5%) is above its solubility limit in a given system (see Table 1 where solubility of 7.5% MCX/6.0% BP3/5.0% OS in this system is 2–2.3%), deposition is greatly enhanced. By contrast, the solubility limit of MCX in the 10% betaine/5% SLS system with 1% perfume is ~3% (In a system with MCX, PP3 and OS, solubility was about 3%; therefore in system with MCX alone, solubility would also be expected to be about 3%). Thus, when only 3% MCX is used, this is solubilized by surfactant and deposition is very low (7).

Examples 6–8 and Comparative

TABLE 4

Effect of polymers dose:

| Example | Comparative<br>Base +<br>Sunscreen<br>0% Jaguar | Comparative<br>Base +<br>Sunscreen<br>0.3% Jaguar | 6<br>Base +<br>Sunscreen<br>0.8% Jaguar | 7<br>Base +<br>Sunscreen<br>1.3% Jaguar | 8<br>Base +<br>Sunscreen<br>1.6% Jaguar |
|---|---|---|---|---|---|
| Betaine | 8 | 8 | 8 | 8 | 8 |
| Isethionate | 3.5 | 3.5 | 3.5 | 3.5 | 3.5 |
| Laureth Sulfate | 3.5 | 3.5 | 3.5 | 3.5 | 3.5 |
| MCX | 7.5 | 7.5 | 7.5 | 7.5 | 7.5 |
| BP3 | 6 | 6 | 6 | 6 | 6 |
| OS | 5 | 5 | 5 | 5 | 5 |
| Crystal. Supp. | 4 | 4 | 4 | | 4 |
| Polymer (Jaguar) | 0 | 0.3 | 0.8 | 1.3 | 1.6 |
| Glycerol | 6 | 6 | 4 | 4 | 6 |
| Perfume | 1 | 1 | 1 | 1 | 1 |
| Water | To 100% | To 100% | To 100% | To 100% | To 100% |
| Deposition | 6 | 24 | 70 | 62 | 66 |

From Examples 6, 7 and 8 and two Comparatives, it can be seen that polymer levels must be used at minimum levels (preferably 0.3% and above, more preferably at least 0.5%, more preferably at least 0.8%) to achieve best deposition results. Jaguar is a preferred polymer although it is not the only which can be used. Preferably, deposition should be at least 10, more preferably at least 14, more preferably at least 20 and more preferably 50 and above.

Examples 9–12

TABLE 5

Effect of type of polymers

| Example | 9<br>Base +<br>Sunscreen +<br>1.3 Jaguar | 10<br>Base +<br>Sunscreen +<br>1.3 JR-400 | 11<br>Base +<br>Sunscreen +<br>Celquat H-100 | 12<br>Base +<br>Sunscreen +<br>1.3% Celquat<br>L-200 |
|---|---|---|---|---|
| Betaine | 8 | 8 | 8 | 8 |
| Isethionate | 3.5 | 3.5 | 3.5 | 3.5 |
| Laureth Sulfate | 3.5 | 3.5 | 3.5 | 3.5 |
| MCX | 7.5 | 7.5 | 7.5 | 7.5 |
| BP3 | 6 | 6 | 6 | 6 |
| OS | 5 | 5 | 5 | 5 |
| OC | | | | |
| Crystal Supp. | | 4 | 4 | 4 |
| Polymer | 1.3 | 1.3 | 1.3 | 1.3 |
| Glycerol | 4 | 6 | 4 | 4 |
| Perfume | 1 | 1 | 1 | 1 |
| Water | To 100% | To 100% | To 100% | To 100% |
| Deposition | 62 | 38 | 16 | 14 |

From these examples it can be seen that, at constant levels, some cationics are better than others at enhancing deposition.

Examples 13–18

TABLE 6

Effect of Sunscreen Cocktails on SPF Deposition and Lather

| | 13<br>18.5%<br>Sunscreen<br>OMC/BP3/<br>OS | 14<br>13.0%<br>Sunscreen<br>OMC/BP3/<br>OS | 15<br>9.0%<br>Sunscreen<br>OMC/BP3/<br>OS | 16<br>14.4%<br>Sunscreen<br>OMC/BP3/<br>OC | 17<br>11.75%<br>Sunscreen<br>OMC/BP3/<br>OC | 18<br>12.0%<br>Sunscreen<br>OMC/<br>Avobenzone |
|---|---|---|---|---|---|---|
| Cocoamido Propyl Betaine | 8.0 | 8.0 | 8.0 | 8.0 | 8.0 | 8.0 |
| Sodium Cocoyl Isethionate | 3.5 | 3.5 | 3.5 | 3.5 | 3.5 | 3.5 |
| Sodium Laureth Sulfate | 3.5 | 3.5 | 3.5 | 3.5 | 3.5 | 3.5 |
| Octyl Methoxy Cinnamate | 7.5 | 5.3 | 37 | 6.75 | 3.75 | 9.0 |
| Benzophenone-3 | 6.0 | 4.2 | 2.9 | 5.4 | 3 | |
| Octyl Salicylate | 5.0 | 3.5 | 2.4 | | | |
| Octocrylene | | | | 9.0 | 5 | |
| Avobenzone | | | | | | 3.0 |
| Crystallization Control Agent | 4.0 | | | | | |
| Guar Hydroxypropyl Trimonium Chloride | 1.6 | 1.6 | 1.6 | 1.3 | 1.3 | 1.3 |
| Glycerol | 6.0 | 6.0 | 6.0 | 4.0 | 4.0 | 4.0 |
| Perfume | 1.0 | 1.0 | 1.0 | 1.0 | 1.0 | |
| Water | To 100% | To 100% | To 100% | To 100% | To 100% | To 100% |
| SPF | 5.2 | 4.5 | 4.7 | 3.8 | 4.1 | 3.6 |
| Deposition | 53 | 50 | 46 | 53 | 47 | 46 |
| Lather | 310 +/− 20 | 312 +− 15 | 315 +/− 19 | | 332 +/− 17 | 291 +/− 20 |

Examples 13–19 again clearly show that, when used above the solubility limits of the various sunscreen cocktail mixtures, deposition, SPF and lather are all significant.

Example 19

TABLE 7

No effect from Crystal Suppressant

| | Base +Sunscreen, 4% Solvent, Few small crystals (10 × 30 μm) | Base + Sunscreen, no Solvent, Huge crystals (20 × 500 μm) |
|---|---|---|
| Cocoamido Propyl Betaine | 8.0 | 8.0 |
| Sodium Cocoyl Isethionate | 3.5 | 3.5 |
| Sodium Laureth Sulfate | 3.5 | 3.5 |
| Octyl Methoxy Cinnamate | 7.5 | 7.5 |
| Benzophenone-3 | 6.0 | 6.0 |
| Octyl Salicylate | 5.0 | 5.0 |
| Octocrylene | 0 | 0 |
| Avobenzone | 0 | 0 |
| Crystallization Suppressant | 4.0 | 0 |
| Guar Hydroxypropyl Trimonium Chloride | 1.6 | 1.6 |
| Glycerol | 6.0 | 6.0 |
| Perfume | 1.0 | 1.0 |
| Water | To 100% | To 100% |
| SPF | 5.2 | 5.2 |
| Deposition | 66 | 53 |
| Lather | 287 +/− 21 | 310 +/− 20 |

This example shows that crystal suppressant has no significant effect on SPF, lather and deposition overall.

Example 20

The following three (3) formulations were used in an in-home test:
Formulation 1
Dove[R] Liquid: No sunscreen.

TABLE 8

| Component | % by Wt. |
|---|---|
| Sodium Cocoyl Isethionate | 6.5 |
| Betaine | 6.0 |
| Amphoacetate | 5.6 |
| SLES | 6.5 |
| Isostearic Acid | 5.0 |
| Silicone | 5.0 |
| Minors (including fragrance, electrolyte, opacifier, preservatives etc.) | ≈1 |
| Water | To balance |

TABLE 9

Formulation 2:

| Ingredient | % by wt. |
|---|---|
| Betaine | 8 |
| Isethionate | 3.5 |
| SLES | 3.5 |
| Octyl Methoxy Cinnamate | 6.75 |
| Benzophenone-3 | 5.4 |
| Octocrylene | 9 |
| Jaguar | 1.3 |
| Glycerol | 4 |
| Perfume | 1 |

TABLE 10

Formulation 3:

| Ingredient | % by wt. |
|---|---|
| Betaine | 8 |
| Isethionate | 3.5 |
| SLES | 3.5 |
| Octyl Methoxy Cinnamate | 6.75 |
| Benzophenone-3 | 5.4 |
| Octocrylene | 9 |
| Jaguar | 1.6 |
| Glycerol | 4 |
| Perfume | 1 |

Results of the three are set forth below:

TABLE 11

| Formulations | SPF |
|---|---|
| Commercial (No Sunscreen) | <1.3 |
| Formulation 2 (21.15% Sunscreen + 1.3% Jaguar) | SPF = 2.14 arm, 2.22 leg |
| Formulation 3 (21.15% Sunscreen + 1.6% Jaguar) | SPF = 2.22 arm, 2.25 leg |

As clearly seen from Table 11 above, when sunscreen is used above solubility limit in surfactant system in combination with cationic, the sun protection delivered was remarkably enhanced.

Results were measured by simple wash under normal use conditions. Panelists were instructed to come to lab within an hour of use to determine MED.

MED was measured on the outer upper arm and the outer upper thigh before and after product use on a panel size of 20 individuals. SPF is calculated from the ratio of MED treated to MED untreated.

What is claimed is:

1. A personal wash cleansing composition comprising:
    (a) 5% to 70% by wt. of a surfactant or surfactants selected from the group consisting of anionic, nonionic, amphoteric or zwitterionic and cationic surfactants wherein at least one surfactant is an anionic surfactant comprising at least 3% by wt. of total composition;
    (b) about 0.3 and above to 5% by wt. of a cationic polymer;
    (c) 5% to 35% by wt. of a sunscreen or mixture of sunscreens;
    wherein the concentration of sunscreen component (c) is above the solubility limit of the sunscreen component in the surfactant system in which said sunscreen component is used;
    wherein the composition has SPF factor of at least 2;
    wherein the sunscreen has deposition of at least 10 $\mu g/cm^2$;
    wherein composition has lather volume of greater than 70 ml using funnel test.
2. A composition according to claim 1, wherein the anionic surfactant comprises at least 5% by wt. of total composition.
3. A composition according to claim 1, wherein the anionic surfactant comprises at least 7% by wt. of total composition.
4. A composition according to claim 1, comprising 0.5% and above cationic polymer.
5. A composition according to claim 4, comprising 0.8% and above cationic polymer.

6. A composition according to claim 1, wherein the cationic polymer is a cationic derivative of guar gum.

7. A composition according to claim 5, wherein the cationic polymer is hydroxy alkyl cationic derivative of guar gum.

8. A composition according to claim. 7, comprising 5 to 30% of the sunscreen or mixture of sunscreens.

9. A composition according to claim 1, wherein sunscreen is selected from the group consisting of alkylmethoxy cinnamate, avobenzone, Benzophenone-3 (2-Hydroxy-4-Methoxybenzophenone), Octyl dimethyl p-aminobenzoic acid, 2,2-di-hydroxy-4-Methoxybenzophenone, ethyl-4-[bis(hydroxypropyl)]aminobenzoate, Octocrylene (2-Ethylhexyl 2-Cyano-3,3-Diphenylacrylate), Octyl Salicylate (2-Ethylhexyl Salicylate), glyceryl aminobenzoate, 3,3,5-trimethylcyclohexylsalicylate, methyl anthranalite, p-dimethylaminobenzoic acid or aminobenzoate, 2-ethyl hexyl p-dimethyl aminobenzoate, 2-phenyl benzimidazole-5-sulfonic acid and mixtures thereof.

10. A composition according to claim 1, having SPF of at least about 2.5.

11. A composition according to claim 10, having SPF of at least about 3.0.

12. A composition according to claim 1, having deposition of at least about 15 $\mu$g/cm$^2$.

13. A composition according to claim 12, having deposition of at least 20 $\mu$g/cm$^2$.

14. A composition according to claim 1, having the lather volume of at least about 110 ml.

15. A composition according to claim 14, having the lather volume of at least about 200 ml.

16. A composition according to claim 15, having the lather volume of at least about 250 ml.

17. A composition according to claim 1, having less than 50% transmittance at a visible wavelength.

* * * * *